United States Patent
Kim

(10) Patent No.: US 7,904,173 B2
(45) Date of Patent: Mar. 8, 2011

(54) FUNCTIONAL METALLICITY ION BAND

(76) Inventor: Kyoung Won Kim, Seoul (KR)

( * ) Notice: Subject to any disclaimer, the term of this patent is extended or adjusted under 35 U.S.C. 154(b) by 152 days.

(21) Appl. No.: 12/086,228

(22) PCT Filed: Mar. 16, 2007

(86) PCT No.: PCT/KR2007/001291
§ 371 (c)(1),
(2), (4) Date: Jun. 3, 2008

(87) PCT Pub. No.: WO2007/108609
PCT Pub. Date: Sep. 27, 2007

(65) Prior Publication Data
US 2009/0306705 A1    Dec. 10, 2009

(30) Foreign Application Priority Data
Mar. 20, 2006    (KR) .................. 10-2006-0025380

(51) Int. Cl.
*A61N 1/18* (2006.01)
(52) U.S. Cl. ........... 607/75; 607/115; 607/145; 607/146; 607/150
(58) Field of Classification Search ............. 607/75, 607/115, 145, 146, 150
See application file for complete search history.

(56) References Cited

U.S. PATENT DOCUMENTS
6,203,562 B1 * 3/2001 Ohkubo ............. 606/204

FOREIGN PATENT DOCUMENTS
JP    2000037437 A * 2/2000

OTHER PUBLICATIONS
English Translation of JP 2000037437 A.*
* cited by examiner

*Primary Examiner* — Niketa I Patel
*Assistant Examiner* — Hiba El-Kaissi
(74) *Attorney, Agent, or Firm* — Blakely, Sokoloff, Taylor & Zafman LLP

(57) ABSTRACT

A pair of functional metal ion bands are provided. The pair of functional metal ion bands are attached to meridians and acupoints of the human body in a simple manner to induce a smooth flow of current in the body, thereby rapidly changing a disease condition to a normal state. The pair of functional metal ion bands comprise a gold-colored thin metal plate as a positive electrode and a silver-colored thin metal plate as a negative electrode wherein the gold-colored thin metal plate is composed of Cu and a metal selected from Ag, Au and Pt and the silver-colored thin metal plate is made of an alloy of Al, Si, Fe, Cu, Mn, Mg and Zn. The pair of functional metal ion bands are manufactured by processing each of the thin metal plates to have a thickness of 1 μm to 1 cm and a diameter of 1 mm to 50 cm, and attaching the processed metal plate to one side of a soft adhesive fabric using an adhesive.

4 Claims, 2 Drawing Sheets

[Fig. 1]
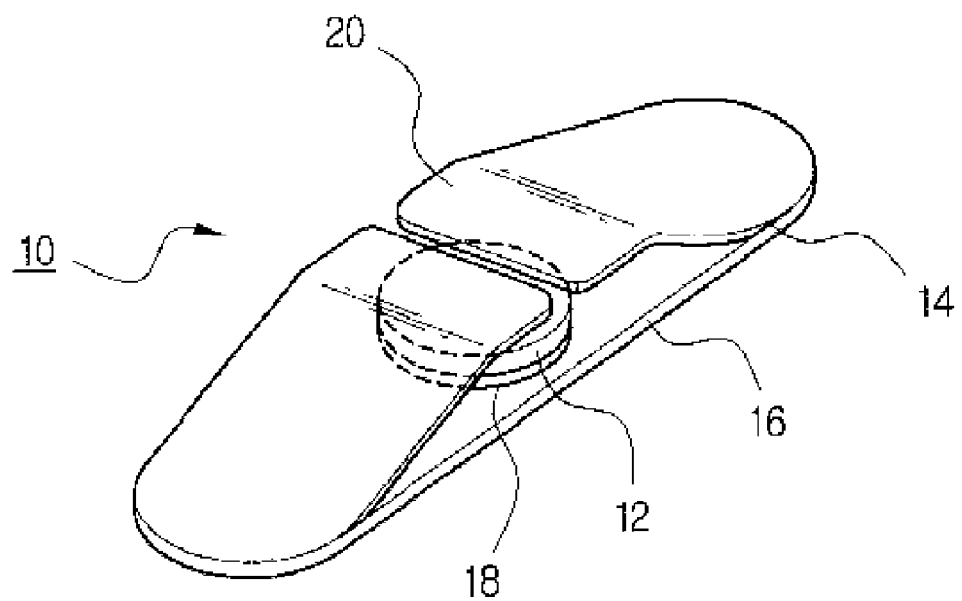
[Fig. 2]
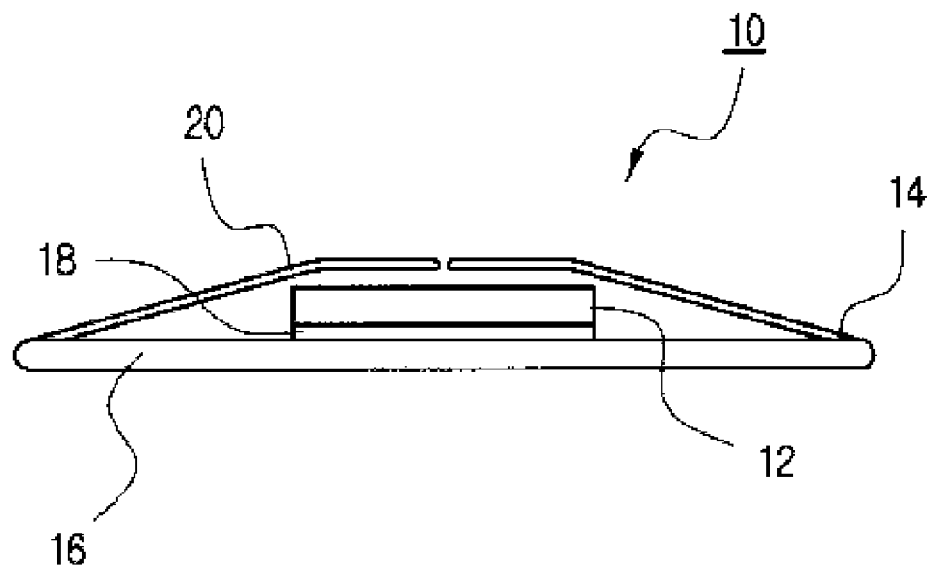

[Fig. 3]
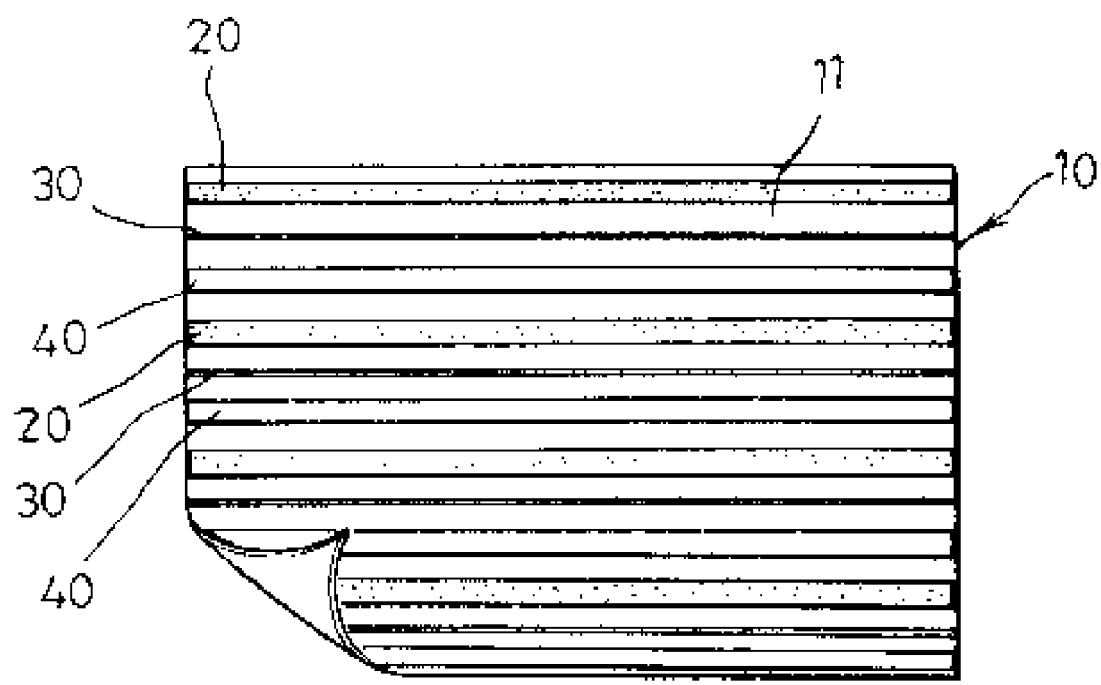

FUNCTIONAL METALLICITY ION BAND

The present patent application is a non-provisional application of International Application No. PCT/KR2007/001291, filed Mar. 16, 2007, now Patent No. KR 100737306.

TECHNICAL FIELD

The present invention relates to functional bands using metal ions (hereinafter, referred to as "functional metal ion bands"). More specifically, the present invention relates to a pair of functional metal ion bands, which comprise metal plates composed of different metal alloy materials, that are simultaneously attached to meridians and acupoints on the hands and feet in a simple manner to induce a smooth flow of current in the body, thereby rapidly changing a disease condition to a normal state.

BACKGROUND ART

A current always circulates through the human body. This current is called a 'body current'. A body current flows well in a healthy person, while no current flows or an excessively large or small amount of current flows in a person who suffers from a disease or has a problem at a particular site, which involves a pain. For example, tetrodotoxin, which is the poison produced by swellfish, inhibits the permeability of sodium ions ($Na^+$) through the cell membranes to block the flow of body current and to paralyze the nervous system, leading to sudden death. Harmful substances, such as heavy metals and polychlorinated biphenyl, block the flow of body current to cause cancers and incurable diseases at a high rate. The flow and blockage of body current may save and lose lives in an instant, respectively.

Sodium ions ($Na^+$) are present at higher concentrations and potassium ions ($K^+$) are present at lower concentrations outside cells than inside. The reason why the ions are present at different concentrations inside and outside cells is that large amounts of $K^+$ and only small amounts of $Na^+$ pass through the cell membranes and pumps operate to absorb $K^+$ inside the cells and discharge $Na^+$ outside the cells. As a result, a current flows at an intracellular voltage of −90 mV to −100 mV in the cells.

Table 1 summarizes body current values and electrical resistance values of the human skin under various conditions.

TABLE 1

|   | Detailed conditions | Current and resistance |
|---|---|---|
| Body current (direct current) | Normal state | 2-5 mA |
|  | Prickly feeling | 30-50 mA |
|  | Muscular dystrophy | 60-90 mA |
|  | Heart failure | 100 mA or above |
| Electrical resistance of human skin | Wet skin | 20,000 Ω |
|  | Dry skin | 1,000 Ω |
|  | Lowest skin resistance | 500 Ω |

Excitation of neurons means that the excited neurons are more electrically negative than other neurons. At this time, a current flows in an opposite direction in the inner portion of the excited neurons. As a result, a circuit is created at the interfaces between the excited neurons. The circuit thus created is referred to as a 'local body circuit', and the current flowing along the circuit is referred to as a 'local current'.

On the other hand, a current induced due to ionization of metals is similar to a body current flowing in the normal state. If a current is allowed to flow through meridians and acupoints as current channels (i.e. pathways of energy introduced from the outside) in the human body, the human body recognizes its state as a normal state, leading to a rapid recovery in response to the current rate.

It is generally known that some pure metals, such as Mg, Al and Zn, and alloys thereof have a higher ionization tendency, while some pure metals, such as Cu, Ag, Pt and Au, and alloys thereof have a lower ionization tendency. Such metals elements and alloys thereof have been used to allow a current to flow through the human body. For example, needles for acupuncture have been used by Oriental medical doctors for the past 2,000 years, and needles for injection have been used by doctors.

However, since the use of needles for acupuncture and injection leaves scars on the human body, there are potential dangers of lethal infectious diseases (e.g., AIDS and hepatitis) through the scars. Under such circumstances, there is a need for a novel method to treat diseases without leaving any scar from the viewpoint of prevention of the diseases.

Ten-won coins (won is a Korean currency unit) composed of copper (65%) and zinc (35%) and hundred-won coins composed of copper (75%) and nickel (25%) are attached to meridians and acupoints to induce the flow of current due to ionization of the metals. However, the use of nickel must be avoided due to the possibility of causing incurable diseases and cancers. In addition, the coins are hard, which causes great inconvenience for patients, are not readily attached to the body, and are bad in appearance. For these disadvantages, many patients are reluctant to use coins.

Particularly, since copper is contained in both ten-won coins and hundred-won coins, a current may flow in an opposite direction, thus resulting in low efficiency.

In recent years, techniques for manufacturing products in which small metal magnets are attached to a band have been developed. For example, Korean Patent No. 221,640 issued to Hwang Hwa Soo, et al. introduces a magnetic patch for medical treatment, based on the principle that various kinds of diseases can be treated by utilizing an electromotive force arising from magnetic tapes and using silver alloy wires and aluminum wires to induce reactions in nerves and muscles. Specifically, as shown in FIG. 3, the magnetic patch comprises a base member 10 having an adhesive part 11, magnetic tapes 20 arranged on the base member, and silver alloy wires 30 and aluminum wires 40 alternately arranged in a row on the adhesive part. The magnetic patch is distinguished from products of the present invention, which are described below, in terms of their usage. That is, the prior art product is attached to a particular site where a patient feels pain, whereas the products of the present invention are attached to acupoints on the hands and feet. In addition, the prior art product is very expensive and is known to exhibit insignificant effects.

DISCLOSURE OF INVENTION

Technical Problem

The present invention has been made in view of the problems of the prior art, and it is a first object of the present invention to provide a pair of functional metal ion bands, which comprise metal plates composed of different inexpensive alloy materials, that allow a current to flow at a higher rate than needles for acupuncture, needles for injection, coins and magnetos utilizing ionization of metals.

It is a second object of the present invention to provide a pair of safe functional metal ion bands that can be attached to meridians and acupoints on the hands and feet in a simple manner to induce a current flow without leaving any scar on the skin, unlike when needles for injection and acupuncture are used.

Technical Solution

In accordance with an aspect of the present invention for achieving the above objects, there is provided a pair of functional metal ion bands, one of which is used as a positive electrode and the other of which is used as a negative electrode, wherein the positive electrode, that is free of Pb, Cd, Hg and hexavalent Cr (which are carcinogenic or cause fatal diseases) and is compliant with the Restriction of Hazardous Substances (RoHS) directive, is produced by blending 51 to 99.96% by weight of electrolytic cathode copper (Cu) having a purity of 99.92% or pure copper having a purity of 99.96% as a basic material with 0.04 to 49% by weight of a metal selected from gold (Au), silver (Ag) and platinum (Pt) to prepare a metal alloy, cold-rolling the metal alloy, cutting the cold-rolled metal alloy into a thin metal plate having a thickness of 1 μm to 1 cm and a diameter of 1 mm to 50 cm, and attaching the metal plate to one side of a soft adhesive fabric using an adhesive, wherein the negative electrode, that is suitable for use in food containers and is compliant with the Restriction of Hazardous Substances (RoHS) directive, is produced by blending 99.3 to 99.7% by weight of aluminum (Al) with 0.01 to 0.3% by weight of silicon (Si), 0.01 to 0.35% by weight of iron (Fe), 0.001 to 0.002% by weight of copper (Cu), 0.001 to 0.003% by weight of manganese (Mn), 0.001 to 0.005% by weight of magnesium (Mg), 0.001% by weight of zinc (Zn), 0.001 to 0.006% by weight of titanium (Ti) and 0.005 to 0.033% by weight of air to prepare a metal alloy material, cold-rolling the metal alloy material, cutting the cold-rolled metal alloy material into a thin metal plate having a thickness of 1 μm to 1 cm and a diameter of 1 mm to 50 cm, and attaching the metal plate to one side of a soft adhesive fabric using an adhesive.

In an embodiment of the present invention, the metal plates of the functional metal ion bands may have a cross section of a circle, a rectangle or a half-moon.

ADVANTAGEOUS EFFECTS

The use of the pair of functional metal ion bands according to the present invention enables rapid, safe and continuous treatment of diseases when compared to the use of needles for acupuncture, needles for injection, coins and magnetos. In addition, the pair of functional metal ion bands according to the present invention can be manufactured at reduced costs. Furthermore, the pair of functional metal ion bands according to the present invention are simultaneously attached to meridians and acupoints on the hands and feet in a simple manner to induce a smooth flow of current in the body without leaving any scar on the skin, unlike when needles for injection and acupuncture are used, thereby rapidly changing a disease condition to a normal state.

BRIEF DESCRIPTION OF THE DRAWINGS

The above and other objects, features and other advantages of the present invention will be more clearly understood from the following detailed description taken in conjunction with the accompanying drawings, in which:

FIG. 1 is a perspective view of one of a pair of functional metal ion bands according to the present invention;

FIG. 2 is a side cross-sectional view of the functional metal ion band shown in FIG. 1; and FIG. 3 is a plan view of a conventional magnetic patch for medical treatment.

BEST MODE FOR CARRYING OUT THE INVENTION

The present invention will now be described in more detail.

FIG. 1 is a perspective view of one of the pair of functional metal ion bands according to the present invention. Since the pair of functional metal ion bands according to the present invention consist of two metal ion bands having the same appearance, only one metal ion band is shown in FIG. 1 for convenience only. FIG. 2 is a side cross-sectional view of the functional metal ion band shown in FIG. 1.

As shown in FIG. 1, the functional metal ion band 10 comprises a disk-type metal plate 12 disposed at its center and an oblong adhesive fabric 16 having adhesive parts 14, to which a pressure-sensitive adhesive is applied, at both edges wherein the metal plate is made of a metal alloy material and the adhesive fabric 16 is made of a soft material, such as a plaster.

The metal plate 12 has a cross section of a circle, as shown in FIG. 1. Although not shown in the figures, the metal plate 12 may have various cross sections, e.g., a rectangle and a half-moon. The soft adhesive fabric 16 has an oblong shape, as shown in FIG. 1. Alternatively, the soft adhesive fabric 16 may have various shapes, e.g., a circle, a rectangle or a half-moon, like the shape of the metal plate.

The metal plate 12 attached to the soft adhesive fabric 16 may be used as a positive or negative electrode. The metal plate 12 as a positive electrode, that is free of Pb, Cd, Hg and hexavalent Cr (which are carcinogenic or cause fatal diseases) and is compliant with the Restriction of Hazardous Substances (RoHS) directive, is produced by blending 51 to 99.96% by weight of electrolytic cathode copper (Cu) having a purity of 99.92% or pure copper having a purity of 99.96% as a basic material with 0.04 to 49% by weight of a metal selected from gold (Au), silver (Ag) and platinum (Pt) to prepare a metal alloy, cold-rolling the metal alloy, and cutting the cold-rolled metal alloy into a thin metal plate having a thickness of 1 μm to 1 cm and a diameter of 1 mm to 50 cm. The metal plate 12 as a positive electrode has a gold color due to the presence of copper (Cu).

The metal plate 12 as a negative electrode, that is suitable for use in food containers and is compliant with the Restriction of Hazardous Substances (RoHS) directive, is produced by blending 99.3 to 99.7% by weight of aluminum (Al) with 0.01 to 0.3% by weight of silicon (Si), 0.01 to 0.35% by weight of iron (Fe), 0.001 to 0.002% by weight of copper (Cu), 0.001 to 0.003% by weight of manganese (Mn), 0.001 to 0.005% by weight of magnesium (Mg), 0.001% by weight of zinc (Zn), 0.001 to 0.006% by weight of titanium (Ti) and 0.005 to 0.033% by weight of air to prepare a metal alloy material, cold-rolling the metal alloy material, and cutting the cold-rolled metal alloy material into a thin metal plate having a thickness of 1 μm to 1 cm and a diameter of 1 mm to 50 cm. The metal plate 12 as a negative electrode has a silver color due to the presence of aluminum (Al).

The magnesium (Mg) content of the metal plate 12 as a negative electrode may be increased to 5.6% by weight, and instead, the aluminum (Al) content of the metal plate 12 may be decreased to 93.705% by weight.

When the content of one of the metal elements constituting the metal plate falls outside the range defined above, the composition of the gold- or silver-colored metal plate is changed, which may be harmful to humans. Therefore, the contents of the constituent metal elements of the metal plate are preferably limited to the respective ranges defined above. The constituent metal elements of the metal plate have a higher ionization tendency, are compliant with the Restriction of Hazardous Substances (RoHS) directive, and are harmless to humans. When the pair of metal ion bands, which comprise the gold-colored metal plate and the silver-colored metal plate, are simultaneously attached to meridians and acupoints on the hands and feet, a smooth flow of current is induced in the body, and as a result, a disease condition is rapidly changed to a normal state.

As shown in FIG. 2, the pair of functional metal ion bands 10 according to the present invention can be manufactured by applying an adhesive 18 to the oblong soft adhesive fabric 16 and attaching each of the gold- and silver-colored metal plates 12 thereon. If desired, a vinyl cover 20 may be used to wholly wrap the functional metal ion band.

The pair of functional metal ion bands according to the present invention can be simultaneously attached to the right hand and the right foot, the left hand and the left foot, the right hand and the left foot or the left hand and the right foot. Particularly, when the metal ion band comprising the silver-colored Al alloy-made metal plate is attached to a meridian or an acupoint on the hands, the metal ion band comprising the gold-colored Cu alloy-made metal plate must be attached to a meridian or an acupoint on the feet. Conversely, when the metal ion band comprising the gold-colored Cu alloy-made metal plate is attached to a meridian or an acupoint on the hands, the metal ion band comprising the silver-colored Al alloy-made metal plate must be attached to a meridian or an acupoint on the feet. That is, the metal ion bands comprising the metal plates attached to the hands and feet must have different colors and compositions. By this configuration, the pair of metal ion bands generate and flow a micro-current in the human body due to ionization of the constituent metals to rapidly change a disease condition to a normal state.

Experimental Example 1

A gold-colored Cu alloy-made metal plate and a silver-colored Al alloy-made metal plate were produced to have the respective compositions defined in the present invention. The two metal plates were dipped in water or a saline solution as an electrolyte in a beaker. Thereafter, a micro-current induced due to ionization of the metals was measured using a Protek 4000 Digital Multimeter (TRUE RMS) at a resistance of 100Ω. This experiment was conducted in a laboratory at the School of Electrical and Electronics Engineering, Chung-Ang University, Korea.

When water was used as an electrolyte, the ionization current was measured to be between 50 μA and 100 μA, which indicates that the ionization potential difference of Cu and Al was in the range of 5 mV to 10 mV. When the skin was dry under the laboratory conditions, the body current at 10 mV was calculated to be 0.5 μA (i.e. I=V/R=10 mV/20,000Ω=0.5 μA). When the skin was wet, the body current at 10 mV was calculated to be 10 μA (i.e. I=V/R=10 mV/1,000Ω=10 μA). At the lowest skin resistance, the body current at 10 mV was calculated to be 20 μA (i.e. I=V/R=10 mV/500Ω=20 μA).

On the other hand, when a saline solution was used as an electrolyte, the ionization current was sharply decreased before and after 1,000 μA and stabilized in the range of 170 μA to 200 μA, which indicates that the ionization potential difference of Cu and Al was in the range of 17 mV to 20 mV. When the skin was dry under the laboratory conditions, the body current at 20 mV was calculated to be 1 μA (i.e. I=V/R=20 mV/20,000Ω=1 μA). When the skin was wet, the body current at 20 mV was calculated to be 20 μA (i.e. I=V/R=20 mV/1,000Ω=20 μA). At the lowest skin resistance, the body current at 20 mV was calculated to be 40 μA (i.e. I=V/R=20 mV/500Ω=40 μA).

In Vivo Experimental Example 1

A gold-colored Cu alloy-made metal plate and a silver-colored Al alloy-made metal plate were produced to have the respective compositions defined in the present invention. The two metal plates were wet with water and a saline solution, respectively. Thereafter, the metal plates were simultaneously attached to meridians and acupoints on the hands and feet. For example, i) in the case of a patient in pain from lung cancer, a band comprising the gold-colored thin metal plate was attached to Kidney Meridian 6 (K 6) of the patient, and at the same time, a band comprising the silver-colored thin metal plate was attached to Lung Meridian 7 (L 7) of the patient; ii) in the case of a patient in pain from breast cancer, a band comprising the gold-colored thin metal plate was attached to Spleen Meridian 4 (Sp 4) of the patient, and at the same time, a band comprising the silver-colored thin metal plate was attached to Pericardium Meridian 6 (P 6) of the patient; iii) in the case of a patient in pain from colon cancer, a band comprising the gold-colored thin metal plate was attached to Kidney Meridian 6 (K 6) of the patient, and at the same time, a band comprising the silver-colored thin metal plate was attached to Lung Meridian 7 (L 7) of the patient; iv) in the case of a patient in pain from lymphoma, a band comprising the gold-colored thin metal plate was attached to Triple Energizer Meridian 5 (TE 5) of the patient, and at the same time, a band comprising the silver-colored thin metal plate was attached to Gall-Bladder Meridian 41 (G 41) of the patient; and v) in the case of a patient in pain from heart failure, a band comprising the gold-colored thin metal plate was attached to Spleen Meridian 4 (Sp 4) of the patient, and at the same time, a band comprising the silver-colored thin metal plate was attached to Pericardium Meridian 6 (P 6). Thereafter, a micro-current flowing through the body was directly measured using a Protek 4000 Digital Multimeter (TRUE RMS).

When the gold-colored Cu alloy-made metal plate and the silver-colored Al alloy-made metal plate were wet with water and a saline solution, respectively, the ionization current values were measured to be in the range of 2 μA to 4 μA, which are the world's lowest recorded values.

The measured current values represent micro-current flowing along acupoints and meridians on the skin without any substantial change in the concentration of body fluids.

The invention claimed is:

1. A kit capable of inducing a flow of current in the body, the kit comprising a pair of metal ion bands which have a gold-colored thin metal plate, as a positive electrode, made of a Cu alloy as a basic material and a silver-colored thin metal plate, as a negative electrode, made of an Al alloy as a basic material, in which the metal plates are respectively bonded on one side of a soft adhesive fabric using an adhesive, wherein the gold-colored thin metal plate is made from a metal alloy material free of Pb, Cd, Hg and hexavalent Cr with a thickness of 1 μm to 1 cm, consisting of 51 to 99.96% by weight of electrolytic cathode copper (Cu) having a purity of 99.92% or pure copper having a purity of 99.96% as a basic material and 0.04 to 49% by weight of a metal selected from gold (Au), silver (Ag) and platinum (Pt), and wherein the silver-colored thin metal plate is made from a metal alloy material with a thickness of 1 μm to 1 cm, consisting of 99.3 to 99.7% by weight of aluminum (Al), 0.01 to 0.3% by weight of silicon (Si), 0.01 to 0.35% by weight of iron (Fe), 0.001 to 0.002% by weight of copper (Cu), 0.001 to 0.003% by weight of manganese (Mn), 0.001 to 5.6% by weight of magnesium (Mg), 0.001% by weight of zinc (Zn), 0.001 to 0.006% by weight of titanium (Ti) and 0.005 to 0.033% by weight of air.

2. The kit according to claim 1, wherein a diameter of the gold-colored thin metal plate is 1 mm to 50 cm.

3. The kit according to claim 1, wherein a diameter of the silver-colored thin metal plate is 1 mm to 50 cm.

4. A kit capable of inducing a flow of current in the body, the kit comprising a pair of metal ion bands which have a gold-colored thin metal plate, as a positive electrode, made of a Cu alloy as a basic material and a silver-colored thin metal plate, as a negative electrode, made of an Al alloy as a basic material, in which the metal plates are respectively bonded on one side of a soft adhesive fabric using an adhesive, wherein the gold-colored thin metal plate is made from a metal alloy material free of Pb, Cd, Hg and hexavalent Cr with a thickness of 1 um to 1 cm, consisting of 51 to 99.96% by weight of electrolytic cathode copper (Cu) having a purity of 99.92% or pure copper having a purity of 99.96% as a basic material and 0.04 to 49% by weight of a metal selected from gold (Au), silver (Ag) and platinum (Pt), and wherein the silver-colored thin metal plate is made from a metal alloy material with a thickness of 1 um to 1 cm, consisting of 93.705% by weight of aluminum (Al), 0.01 to 0.3% by weight of silicon (Si), 0.01 to 0.35% by weight of iron (Fe), 0.001 to 0.002% by weight of copper (Cu), 0.001 to 0.003% by weight of manganese (Mn), 5.6% by weight of magnesium (Mg), 0.001% by weight of zinc (Zn), 0.001 to 0.006% by weight of titanium (Ti) and 0.005 to 0.033% by weight of air.

\* \* \* \* \*